US006588020B1

(12) United States Patent
Stewart, III et al.

(10) Patent No.: US 6,588,020 B1
(45) Date of Patent: Jul. 8, 2003

(54) BACK SUPPORT DEVICE WITH SURGICAL AREA PROTECTION

(75) Inventors: Kenneth G. Stewart, III, Sarasota, FL (US); Thomas Sweeney, Sarasota, FL (US)

(73) Assignee: The Idea People LLC, Sarasota, FL (US)

( * ) Notice: Subject to any disclaimer, the term of this patent is extended or adjusted under 35 U.S.C. 154(b) by 0 days.

(21) Appl. No.: 10/024,192

(22) Filed: Dec. 21, 2001

(51) Int. Cl.[7] .................................................. A61F 5/00

(52) U.S. Cl. ...................................... 2/94; 5/624; 2/267

(58) Field of Search ................................ 2/44, 92, 455, 2/462, 465, 467, 267, 311, 312, 338, 102; 5/1, 600, 621, 624, 630, 633, 648, 652, 653, 654, 657; 602/19, 60, 61; 297/112; 128/112.1, 113.1, 116.1, 125.1, 870, 871, 876, 95.1, 99.1, 100.1, 101.1, 106.1, 107.1; 607/96, 108, 112, 114

(56) References Cited

U.S. PATENT DOCUMENTS 4,189,182 A * 2/1980 Rhoe ............................ 5/653
4,676,247 A 6/1987 Van Cleve
4,702,235 A 10/1987 Hong
4,837,859 A 6/1989 Hamberg
5,062,414 A 11/1991 Grim
5,146,625 A 9/1992 Steele et al.
5,179,942 A 1/1993 Drulias et al.
5,297,293 A * 3/1994 Obujen ........................ 2/44 X
5,305,471 A 4/1994 Steele et al.
5,314,455 A 5/1994 Johnson, Jr. et al.
5,410,755 A * 5/1995 Obujen ........................ 2/44 X
5,551,085 A * 9/1996 Leighton ......................... 2/44
5,665,057 A * 9/1997 Murphy ....................... 602/19
5,797,143 A * 8/1998 Buxton .......................... 2/102
5,928,275 A * 7/1999 Yates et al. ................ 607/112
5,948,013 A 9/1999 Swezey et al.
5,984,951 A * 11/1999 Weiss et al. ................ 607/112

* cited by examiner

*Primary Examiner*—G Hale
(74) *Attorney, Agent, or Firm*—Barnes & Thornburg

(57) ABSTRACT

A portable back support device for providing vertebrae decompression support and therapeutic heating and/or cooling while preventing pressure against an incision or injured portion of the back. The support device can be made adjustable to fit different size persons.

27 Claims, 1 Drawing Sheet

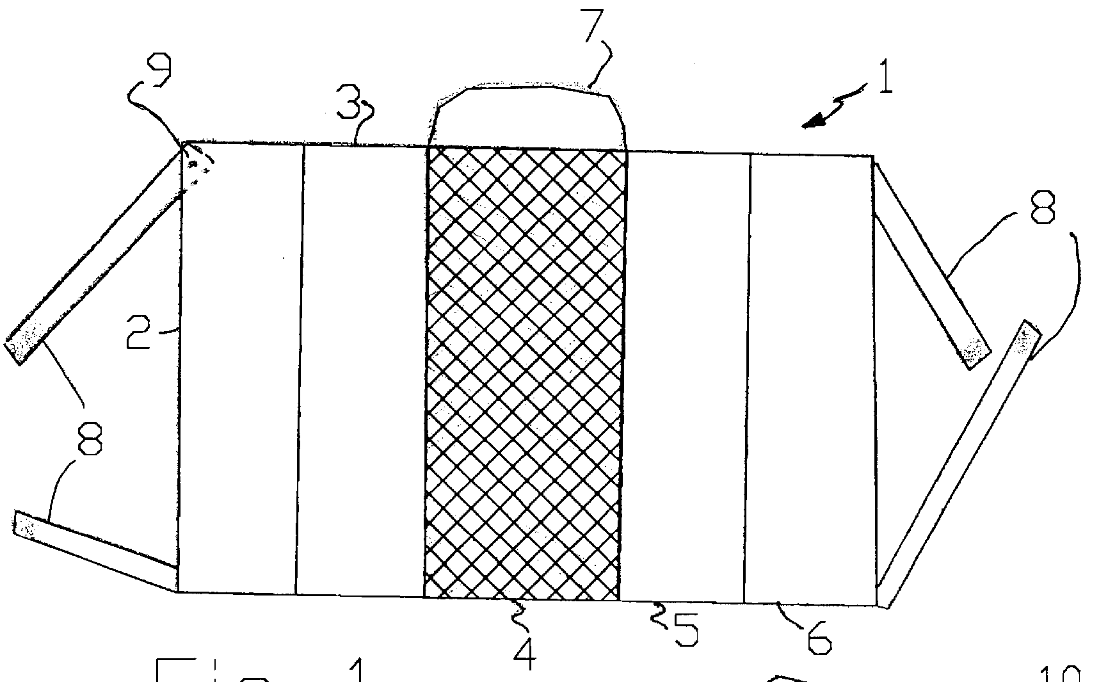
Fig 1
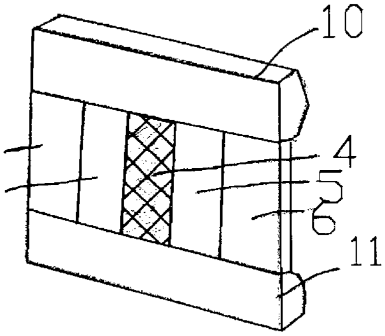
Fig.2
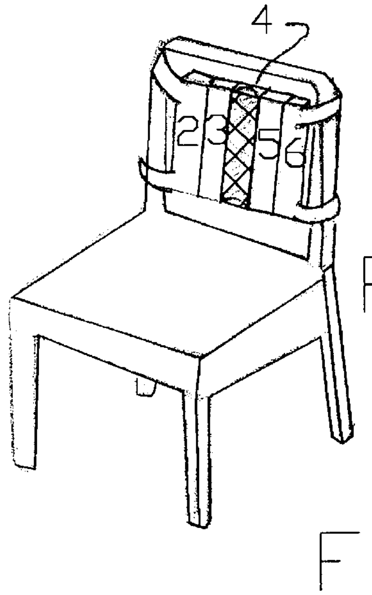
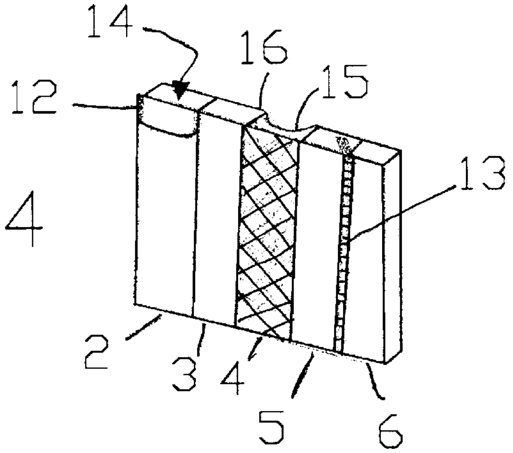
Fig.4
Fig.3

BACK SUPPORT DEVICE WITH SURGICAL AREA PROTECTION

BACKGROUND OF THE INVENTION

1. Field of the Invention

The invention relates to a back support device which applies supportive pressure to desired areas of a person's back in a manner which protects a prescribed area of the back from pressure due to contact with other objects.

More particularly, the invention relates to an adjustable back support device which is portable and can be used basically anywhere, in any setting as needed to provide support for a person's back while avoiding the application of pressure or contact in a sensitive area such as where surgery has been performed. The device is useful for persons recovering from back surgery or those with a back injury.

2. Description of the Related Technology

U.S. Pat. No. 5,547,251 discloses a wheel chair having a sling construction back support and a cushioning arrangement for providing support to the side of the sling opposite the person's back. The cushioning arrangement is configured to modify the support provided by the sling. The cushioning arrangement adjusts the distribution of support provided to the occupant by the upholstery of the backrest to contour the sitting profile of the wheelchair occupant. The cushioning arrangement does not contact the person's back, but modifies the support provided by the sling.

U.S. Pat. No. 5,146,625 discloses a protective vest having cooling means comprising a plurality of elongated pockets on front and back panels, each of which has an opening to receive a cooling pack into the pocket. In one embodiment, each pocket has inner and outer walls with a structural layer and an insulation layer. The insulation layer of the inner wall inhibits too rapid cooling of the user's torso which might otherwise occur during cooling by the gel packs. The vest is not designed to distribute pressure as described with respect to the present invention.

U.S. Pat. No. 5,062,414 discloses a back brace of elastic material which carries a gel pad and an air bladder with three individually inflatable chambers, including left, right, and overall areas, so that the user may adjust the pressure exerted on the pad and hence the support of the lower back. The gel pad may also contain an adjustable heating element to electrically heat the gel-like material. The back brace does not have a panel which applies pressure except in a prescribed area and which relieves spinal pressure.

SUMMARY OF THE INVENTION

The invention is directed to a portable back support device for applying back supportive pressure selectively such that a confined area is not subject to the supportive pressure of the other areas. The device also assists in reducing gravitational, or other, compression of the vertebrae in a person's spine.

Other objects, advantages and novel features of the present invention will become apparent from the following detailed description of the invention when considered in conjunction with the accompanying drawings.

BRIEF DESCRIPTION OF THE DRAWINGS

FIG. 1 shows a plan view of one embodiment according to the invention.

FIG. 2 shows a perspective view of a second embodiment of the invention.

FIG. 3 shows the invention attached to a chair.

FIG. 4 is a perspective view showing additional advantageous aspects of the invention.

DETAILED DESCRIPTION OF THE PREFERRED EMBODIMENT

The preferred embodiment of the invention provides a vest-like support device which is designed to be strapped around the waist or over the shoulders. The device is easily adjustable by adding or removing panels to add width or length, thus accommodating persons of different size. The panels depicted in the drawing are of similar size and shape, however, it should be evident that panels of different lengths, widths and shapes are contemplated. The device is generally shaped to fit the human torso and covers the back from shoulders to hips. The device includes structure which prevents pressure on a prescribed back area, such as an area which has been sutured or is otherwise recovering from injury or surgery. Contact with a sutured healing area can also cause irritation and prevents contact with air that promotes healing.

The supportive device is also designed to relieve pressure on a person's vertebrae.

A person recovering from back surgery must be able to sit or lie in a back resting position without having pressure against the surgically recovering portion of the vertebrae. This is important for people recuperating at home and can be particularly important for persons who have returned to work and perform desk work such as secretaries, draftsmen, and the like whose seating arrangements would otherwise press against the back area where surgery has been performed.

The present invention provides a portable support device which may be used to provide acceptable support and comfort for a person while seated or lying down.

An optional feature is to provide a back support device that relieves compressive forces on the vertebrae.

A further additional feature is providing a sleep garment which protects a portion of a person's back (having stitches, etc.) from pressures and contact with different objects encountered when lying prone and turning while asleep.

Yet another aspect of the invention is that it allows mobility for persons recovering from, for example, spine surgery whereby they are able to use mass transit, their own personal automobile, etc. so as to be able to lean back against a seat or other support without pressure on, or contact with, portions of the person's back side.

The device also provides hot or cold pressure to assist in recovery from back surgery or to relieve back discomfort.

As seen in FIG. 1 of the drawing there is shown a device or garment 1 having five vertically extending panels. The garment is made out of a typically light-weight but strong fabric like nylon, polyester or similar material. Portions of the garment may be of an elastic material to provide a better fit. The five panels 2–6 may be sewn together or releasably fastened together. In this construction of the center panel 4 it is generally air permeable so that air can promote healing of the affected area. The center panel 4 is made of two layers of thin mesh-like material with the space between the layers being accessible for insertion and removal of an absorbent pad or dressing 7. Pad 7 may reside between the mesh layers, be hung on the mesh on the side next to the person or be affixed (taped, etc.) to the person over the sutured incision.

The panels 2–3 and 5–6 on either side of the center panel 4 have a thickness of ½ inch to three inches greater than the thickness of the center panel. All of the panels need not be of the same thickness. It is best if the thickest panels are adjacent the center panel. Thus, for example, mesh panel 4 is the thinnest, panels 3 and 5 the thickest and panels 2 and 6 of a lesser thickness than panels 3 and 5. These side panels are made of two layers of material joined together along three sides with the fourth side open such that a pocket is formed (see FIG. 4). With the pocket being recessed from the front, no undesirable contact with the person's anatomy at that location occurs.

The pocket may be filled with an inflatable bag, with foam rubber or provided with a hot/cold gel pack. A suitable gel thermal pack that may be heated or cooled is described in U.S. Pat. No. 4,756,311. The panels and pockets may vary in shape, size and number.

When the garment is placed on a persons back such that the center panel overlies the vertebrae the thickness of the adjacent panels prevents pressure on the center panel area when the person is seated or lying down. The pressure against the persons back is against the thicker side panels, not the portion of their back covered by the center panel 4. Thus the center panel will cover an incision area while at the same time avoiding pressure being applied to the incision area. The difference in thickness between the center and adjacent panels is great enough to permit a dressing to cover the sutured area without pressure.

Straps 8 are also shown in FIG. 1 connected to the corners of the back support device. Four straps are shown, but additional, or fewer, straps may be used to assist in firmly positioning the garment. A pivot 9 is shown in FIG. 1 connecting one of the straps (some or all of the straps may have pivots) to permit the strap to change the direction it can be wrapped around a human torso or furniture part. Because the device is made of fabric-like material and the pocket inserts are of material that will conform to shapes like a person's torso or even most chairs, it can be strapped tightly. For example, as when the back support is wrapped around a person the upper-left and lower-right straps can be joined and the upper-right and lower-left straps also joined thus forming a cross or "X" shape on the person's chest and abdomen. The strap lengths are adjustable and the ends are provided with fasteners for joining to another strap. As can be readily seen this permits the support device to be firmly attached to a human torso or to other objects like a furniture part.

FIG. 2 depicts an embodiment of the invention wherein there are two horizontal panels 10 and 11 which are tapered so that when the person leans against the panels they tend to separate. This is advantageous when the separation is in a direction along the vertebrae since it provides a gentle decompression force on the spine. The taper shown is exaggerated for illustration purposes. A gentle taper is preferred.

FIG. 3 shows the device fixed to a chair. This is advantageous for persons who may frequently leave and return to the same chair. If the back support device is fixed to the chair the person can return to the chair and be seated with the back support in place to provide the necessary cushion.

As best seen in FIG. 3, panel 4 is shaped to accept tensional loading but not compression loading. The layer of fabric on the side adjacent the person's back is longer between panels 3 and 5 than the layer of fabric on the opposite side of panel 4. This permits the panels to be stretched apart, or horizontally as seen in FIG. 3, so that the back layer of panel 4 is taut (absorbs tensional loading) while the inner layer is loose to allow air circulation and prevent the application of pressure (does not permit compression) to that area of the person's anatomy.

As shown in FIG. 4 each of the panels can be provided with a space 14 for heating and/or cooling means (not shown). Various types of heating or cooling means are known, including gel packs, ice packs, resistance heating means, etc. As seen in FIG. 4 panel 2 has an open top side (or end) which is provided with a flap 12 having securement to firmly close the pocket. When the flap 12 is folded over the top and secured to the opposite side of the panel the contents of the panel are held firmly in place. Securement can be by any conventional means such as a button/hole arrangement, buckle/clasp, zipper or hook and loop fasteners, e.g., VELCRO. As previously described the panels may be sewn together or releasably fastened together as by zippers. Zipper 13 is shown fastening panels 5 and 6. Of course some panels may be fixedly attached whereas others may be releasably attached. It is also evident from FIG. 4 that mesh layer 15 for abutting the persons back may have a greater length between the adjacent panels 3 and 5 than the outer mesh layer 16. This ensures that the mesh doesn't press against the back in the area where low, or no, pressure is desired.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A portable back support device for applying pressure to an area of a person's back while substantially elimniating pressure form a prescribed area of the back comprising, at least one first panel and a plurality of second panels all connected to form a cover shaped to be placed on the back of a human torso, the first panel formed by a recessed covering for facing the prescribed area of the person's anatomy and a second covering spaced rearwardly from and shorter than the recessed covering so as to allow the first panel to accept tensional loading but not comapressional loading, the plurality of second panels each having a thickness greater than the first panel, and fasteners connected to the first and/or second panels for securing the device in a position to enable supportive pressure to be applied to a desired first back area without applying any supportive pressure to the prescribed area.

2. The device of claim 1 wherein at least one of the second panels has one or more pockets for removably inserting a pack of a hot or cold temperature retaining material.

3. The device of claim 2 wherein the temperature retaining material is a heated or cooled gel pack.

4. The device of claim 1 wherein the panels are arranged and designed to apply decompressive forces to the vertebrae.

5. The device of claim 1 wherein the fasteners are straps for firmly holding the device in place.

6. The device of claim 5 wherein the straps firmly hold the device to a furniture part.

7. The device of claim 5 wherein the straps firmly hold the device to a human torso.

8. The device of claim 1 wherein the straps are adjustable.

9. The device of claim 8 wherein the adjustability is provided by hook and loop type closures.

10. The device of claim 1 having adjustment for expanding, or contracting, the back support device to accommodate persons of larger, or smaller, girth and taller or shorter persons.

11. A portable back support device for applying pressure to an area of a person's back while substantially eliminating pressure from a prescribed area of the back comprising, at least one first panel and a plurality of second panels all connected to form a cover shaped to be placed on the back of a human torso, the first panel forming a recessed covering for the prescribed area of the person's anatotny and being shaped to accept tensional loading but not compressional loading, the plurality of second panels each having a thickness greater than the first panel, fasteners connected to the first and/or second panels for securing the device in a position to enable supportive pressure to be applied to a desired first back area without applying any supportive pressure to the prescribed area, and wherein panels can be added or removed.

12. The device of claim 1 wherein at least two of the second panels adjacent the first panel are at least ½ to three inches thicker than the first panel.

13. A portable back support device for applying pressure to an area of a person's back while substantially eliminating pressure from a prescribed area of the back comprising, at least one first panel and a plurality of second panels all connected to form a cover shaped to be placed on the back of a human torso, the first panel forming a recessed covering for the prescribed area of the person's anatomy and being shaped to accept tensional loading but not compressional loading, the plurality of second panels each having a thickness greater than the first panel, fasteners connected to the first and/or second panels for securing the device in a position to enable supportive pressure to be applied to a desired first back area without applying any supportive pressure to the prescribed area, and wherein at least one of the second panels tapers in thickness with the thickest being adjacent the first panel.

14. A portable back support device for applying pressure to an area of a person's back while substantially eliminating pressure from a prescribed area of the back comprising, at least one first panel and a plurality of second panels all connected to form a cover shaped to be placed on the back of a human torso, the first panel forming a recessed covering for the prescribed area of the person's anatomy and being shaped to accept tensional loading but not compressional loading, the plurality of second panels each having a thickness greater than the first panel, fasteners connected to the first and/or second panels for securing the device in a position to enable supportive pressure to be applied to a desired first back area without applying any supportive pressure to the prescribed area, and wherein the first panel has a support for removably holding a dressing.

15. The device of claim 1 wherein the first and second panels are arranged so that the supportive pressure is applied to the first back area which is on two sides of the prescribed area.

16. The device of claim 1 wherein the first and second panels are arranged so that the supportive pressure is applied to the first back area which substantially surrounds the prescribed area.

17. The device of claim 1 wherein at least a portion of one of the panels is made of an elastic material to provide a better fit.

18. The device of claim 1 wherein the first panel comprises an air permeable member.

19. A portable back support device for applying pressure to an area of a person's back while substantially eliminating pressure from a prescribed area of the back comprising, at least one first panel and a plurality of second panels all connected to form a cover shaped to be placed on the back of a human torso, the first panel comprising an air permeable material forming a recessed covering for the prescribed area of the person's anatomy and being shaped to accept tensional loading but not compressional loading, the plurality of second panels each having a thickness greater than the first panel, with each second panel being at least ½ to three inches thicker than the first panel, at least two of the second panels being thicker than any other panels and being adjacent the first panel, and fasteners connected to the first and/or second panels for securing the device in a position to enable supportive pressure to be applied to a desired first back area without applying any supportive pressure to the prescribed area.

20. The device of claim 19 wherein at least one of the second panels has one or more pockets containing a removable pack of a hot or cold temperature retaining applying therapeutic thermal treatment.

21. A portable back support device for applying pressure to an area of a person's back while substantially eliminating pressure from a prescribed area of the back comprising, at least one first panel and a plurality of second panels all connected to form a cover shaped to be placed on the back of a human torso, the first panel comprising an air permeable material forming a recessed covering for the prescribed area of the person's anatomy, the plurality of second panels each having a thickness greater than the first panel, and fasteners connected to the first and/or second panels for securing the device in a position to enable supportive pressure to be applied to a desired first back area without applying any supportive pressure to the prescribed area.

22. The device of claim 19 wherein at least one of the second panels has one or more pockets for removably inserting a pack of a hot or cold temperature retaining material.

23. The device of claim 21 wherein at least one of the second panels has one or more pockets for removably inserting a pack of a hot or cold temperature retaining material.

24. The device of claim 19 with the cover having adjustment for expanding, or contracting, the back support device to accommodate persons of larger, or smaller, girth and taller or shorter persons.

25. The device of claim 21 with the cover having adjustment for expanding, or contracting, the back support device to accommodate persons of larger, or smaller, girth and taller or shorter persons.

26. The device of claim 19 wherein at least two of the second panels adjacent the first panel are at least ½ to three inches thicker than the first panel.

27. The device of claim 21 wherein at least two of the second panels adjacent the first panel are at least ½ to three inches thicker tan the first panel.

* * * * *